United States Patent [19]

Baxter et al.

[11] Patent Number: 5,068,205

[45] Date of Patent: Nov. 26, 1991

[54] HEADER MOUNTED CHEMICALLY SENSITIVE ISFET AND METHOD OF MANUFACTURE

[75] Inventors: Ronald D. Baxter, Furlong; Paul M. Kroninger, Jr., North Wales, both of Pa.

[73] Assignee: General Signal Corporation, Stamford, Conn.

[21] Appl. No.: 357,505

[22] Filed: May 26, 1989

[51] Int. Cl.⁵ .............................................. H01L 21/58
[52] U.S. Cl. .................................... 437/205; 437/215; 437/925; 437/226
[58] Field of Search ................. 204/416; 437/51, 205, 437/214, 215, 925, 226; 357/25; 174/52.5; 228/180.1, 180.2

[56] References Cited

U.S. PATENT DOCUMENTS

| | | | |
|---|---|---|---|
| 3,280,019 | 10/1966 | Harding et al. | 204/181 |
| 3,489,958 | 1/1970 | Gramberg et al. | 317/234 R |
| 3,579,815 | 5/1971 | Gentry | 29/580 |
| 3,694,707 | 9/1972 | Nakamura et al. | 317/235 R |
| 3,731,159 | 5/1973 | McCann | 317/234 R |
| 3,913,126 | 10/1975 | Hooker et al. | 357/52 |
| 3,943,555 | 3/1976 | Mueller et al. | 357/49 |
| 4,040,084 | 8/1977 | Tanaka et al. | 357/55 |
| 4,124,863 | 11/1978 | Mason | 357/54 |
| 4,364,078 | 12/1982 | Smith et al. | 357/52 |
| 4,505,799 | 3/1985 | Baxter | 204/416 |
| 4,541,000 | 9/1985 | Colquhoun et al. | 357/15 |
| 4,568,445 | 2/1986 | Cates et al. | 204/416 |
| 4,874,499 | 10/1989 | Smith et al. | 204/403 |

FOREIGN PATENT DOCUMENTS

| | | | |
|---|---|---|---|
| 2736200 | 2/1979 | Fed. Rep. of Germany | 357/25 |
| 55-024603 | 2/1980 | Japan | 357/25 |
| 89336219 | 3/1988 | Japan | 357/25 |

OTHER PUBLICATIONS

"Chip Carrier", *IBM Technical Disclosure Bulletin*, vol. 32, No. 10A, Mar. 1990.

Primary Examiner—Olik Chaudhuri
Assistant Examiner—G. Fourson
Attorney, Agent, or Firm—William G. Miller, Jr.

[57] ABSTRACT

This invention provides a method for producing header mounted sensors, such as a chemically sensitive ISFET structures, which comprises steps which include providing a plurality of electrochemically sensitive ISFET sites on a semiconductor substrate with a source region, a drain region and an electrochemically sensitive gate region on the front of said substrate with contacts for said regions on the back of the substrate. A glass carrier, such as borosilicate glass is provided for the substrate. The carrier has a hole in it to maintain uncovered the contact areas of the ISFET sites and the carrier also has leads to provide electrical access to the area of the holes from the edges of the carrier. The substrate is electrostatically bonded to the glass carrier at the periphery of each of the ISFET sites and the boundaries of the individual ISFET sites are V-groove etched to form isolated individual silicon mesas each representing an individual ISFET structure. After formation of the individual mesas a passivation coating is deposited over the front of the substrate in a manner which will not obviate the chemical sensitivity of the gate region. There is then provided electrical contact from the contact areas of the ISFET to the metallized electrical leads of the carrier and the wafer is then diced at the site boundaries to produce individual chemically sensitive ISFET structures.

8 Claims, 6 Drawing Sheets

HEADER MOUNTED CHEMICALLY SENSITIVE ISFET AND METHOD OF MANUFACTURE

BACKGROUND OF THE INVENTION

This invention relates to chemically sensitive sensors such as ISFETs for use in the detection and measurement of chemical properties and a method for the manufacture of header mounted sensors for use in measuring probes. The term "chemically sensitive" as used herein, shall be understood to include sensitivity to ion activity and the presence, concentration and activity of any of a variety of chemical and biochemical substances. The term header is used to mean the structure for physically supporting sensor elements, such as ISFETs, as well as for providing the electrical contacts from the outside to the sensor, such as to the substrate, source and drain regions of an ISFET. Typical header structures are too small for easy handling in industrial applications and are therefore usually mounted in a larger body structure so that the combination makes up what is referred to herein as a probe.

When used as a pH sensor, for example, an ISFET must be mounted on a header of some sort, not only as a support, but also as a means for sealing the ISFET itself, except for the chemically sensitive region, from the electrolyte being measured. This sealing will thus provide environmental interfacing of the ISFET and the ambient electrolyte. The header assembly is then mounted in a probe body structure which is either permanently mounted for immersion in the electrolyte or hand held for immersion.

The electrolytes being measured are normally a very hostile environment for electrical circuit elements. It is, therefore, desirable to have the sensor so constructed as to minimize contact between the associated electrical circuit elements and the electrolyte solution so that the integrity, stability, and reliability of the device is maintained. I have previously solved this problem as it relates to an individual ISFET chip, particularly the source and drain region contacts, by etching holes from the back of the ISFET to the source and drain regions with sidewall isolation provided in those holes and a metallization of the surface of those sidewalls to provide a connection between the source and drain regions and contact pads or areas on the back of the ISFET. The back of the ISFET was then protected by the body of the probe in which the ISFET was mounted. One form for such a structure and a method for manufacturing it is disclosed in U.S. Pat. No. 4,505,799, issued to me on Mar. 19, 1985. That patent is hereby incorporated by reference as a part of the present specification.

As mentioned above, and as shown in FIGS. 3, 4 and 5 of the referenced patent, it is necessary to mount the ISFET chip in a probe assembly which will adapt it for the particular type of measurement intended. In the referenced patent this mounting involves the mounting of the ISFET chip on a header or support member, such as a piece of aluminum oxide or borosilicate glass, and dielectrically isolating the edges of the chip by coating the edges with epoxy. As described, the chip may be bonded to the header or support member by use of epoxy or by anodic bonding if the header is borosilicate glass. The isolation of the sidewalls of the chip and the mounting on the header, when carried out on the individual ISFET chips, as in this patent, is an expensive and time consuming procedure which does not lend itself to mass production at low cost. Furthermore, it would be more desirable to provide an inorganic (dielectric) protection which would be more durable under the adverse conditions of high temperature and high pH. Such protection is difficult or uneconomical to apply at the chip stage of manufacture, however.

It is an object of this invention to provide a method for easily and inexpensively manufacturing header mounted solid state chemically sensitive sensors, such as ISFET structures useful for pH probe assemblies, which will have the sidewalls of the silicon chip on which the sensors are formed dielectrically isolated from the solution to be tested and which will provide contacts for the sensor, such as for the source and drain regions of an ISFET, as well as a substrate contact, in a manner such that those contacts will not be exposed to the solution to be tested when the header is mounted in a probe assembly.

SUMMARY OF THE INVENTION

To accomplish the objects of the invention there is provided a header mounted sensor structure and a method for producing such structures. The method includes providing a plurality of electrochemically sensitive sensor sites on a semiconductor substrate, each site has a chemically sensitive region on the front of the substrate with associated electrical contact pads on the back of the substrate. A borosilicate glass carrier is provided to support the substrate. The carrier has holes which serve to maintain uncovered the contact areas on the back of the sensors sites. The carrier also has metallized areas which serve as lead-outs to provide electrical access to the area of each hole from an edge of the carrier. The substrate is bonded, as by anodic bonding, to the glass carrier at the periphery of each of the sensor sites and the boundaries of the individual sensor sites are V-groove etched to form isolated individual silicon mesas, each representing an individual sensor structure. After formation of the individual mesas a passivation coating is deposited over the front of the substrate in a manner which will not obviate the sensitivity of the chemically sensitive regions of the sensors. There is then provided electrical contact from the contact pads of the sensor to the metallized electrical lead-outs of the carrier. The carrier mounted sensors are then bonded, as by anodic bonding, to a silicon cover plate which has a channel to accommodate each set of lead-outs. The resulting wafer is then diced at the site boundaries to produce individual, header mounted, chemically sensitive sensors.

BRIEF DESCRIPTION OF THE DRAWINGS

In the drawings, in which like reference characters refer to like elements.

DESCRIPTION OF THE PREFERRED EMBODIMENT

Figures 1, 3:
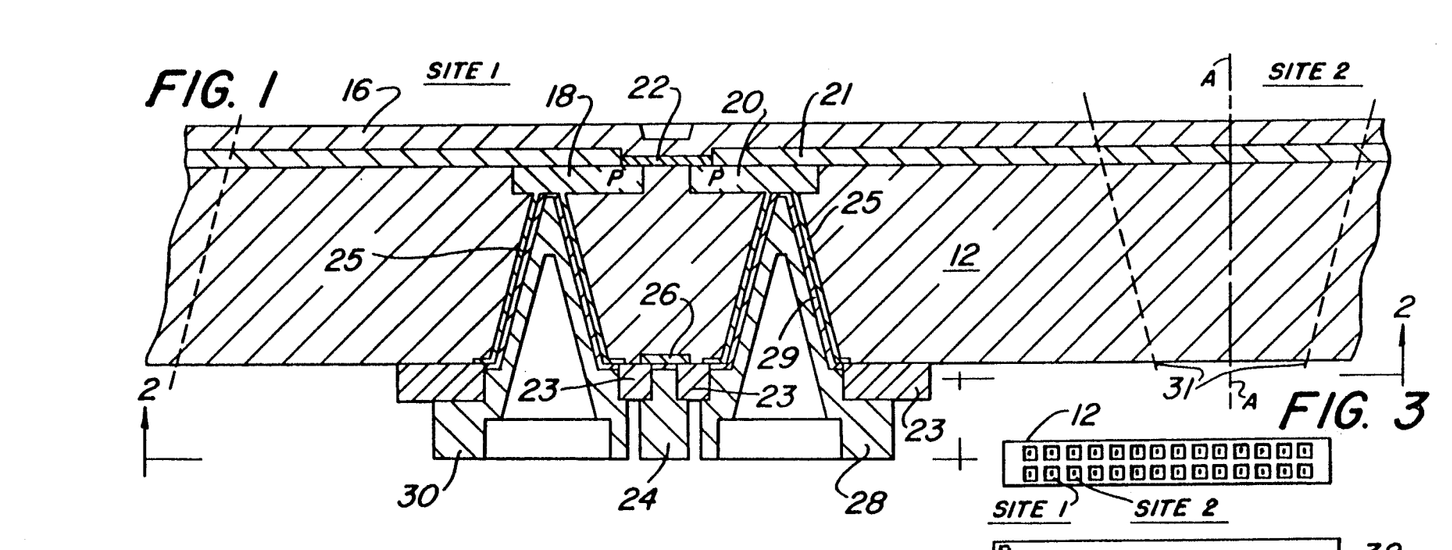
FIG. 1 is a cross-section showing the structure of a single ISFET site of a multisite substrate.
FIG. 3 is a plan view of the top or front of a substrate having 28 ISFET sites aligned in two parallel rows.

There is shown in FIG. 1 a cross-section of a part of an ISFET wafer having a plurality of sites, each of which contains an individual ISFET structure which is generally constructed in accordance with the process described in my U.S. Pat. No. 4,505,799. In accordance with the process of that patent, the ISFETs of the present FIG. 1 are constructed on an N-type silicon substrate 12, which has an orientation of (100). On the front side, the substrate is shown as being coated with a field oxide 21, which corresponds to the plurality of oxide coatings shown in the referenced patent. The substrate is doped to have P+ drain regions, such as 18 in site 1, and P+ source regions, such as 20 in site 1. In the area between the source and drain for each site, there is a window in the field oxide 21 where a gate oxide 22, as shown for site 1, has been grown under the ion sensitive membrane 16, of material such as $Ta_2O_5$.

On the back of the substrate 12, there is a field oxide coating 23 which has been patterned to have a circular outline and is windowed to provide the substrate contact pad 24 to an N+ region 26, as shown for site 1. Other windows are provided for the source contact pad 28 and the drain contact pad 30, as shown for site 1. The drain and source contact is made through the surface metallization of holes etched in the back of the ISFET. The metallization may be with aluminum, for example. The holes are pyramidal in shape, as will be evident from other figures. The sidewalls of the holes are provided with an isolating P+ region, such as 25, for the holes leading to drain 18 and source 20. The isolation is needed to electrically isolate the substrate from the metallization deposited in each of the holes as necessary to provide the electrical contact from the back of the ISFET chip to the drain 18 and the source 20. As will be evident from the figures, the metallization is carried over the sidewalls of the etched holes onto the back to provide contact areas or pads for providing the necessary lead connections for the drain and source when the ISFET chip is incorporated into a header. Good electrical contact between the metallization and the isolating P+ regions 25 is provided by a platinum silicide layer 29, not shown in the method described in U.S. Pat. No. 4,505,799, which is laid over the isolating regions before the deposition of the metallization.

Figure 2:
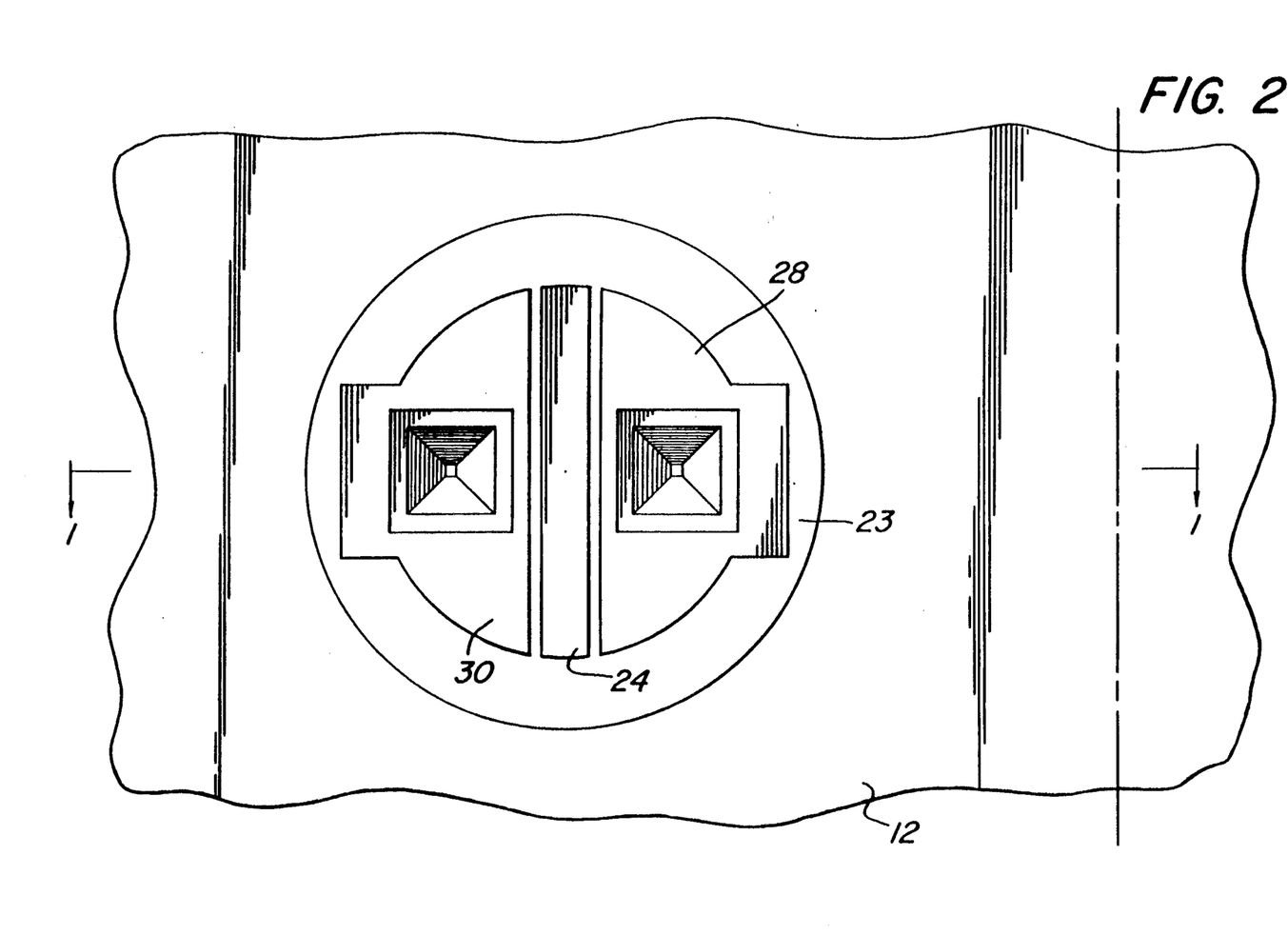
FIG. 2 is a plan view of the bottom or back of the substrate of FIG. 1 showing details of that side of the substrate.

FIG. 2 illustrates a plan view of the back of the ISFET site 1, taken along line 2—2 of FIG. 1. Here, the pyramidal shape of the holes etched to the drain and source regions are evident, as is the circular outline of the field oxide pattern on the back of the substrate.

FIG. 3 is a plan view of the top of an entire wafer of silicon with 28 ISFET sites located in two parallel rows. Sites 1 and 2 are identified as typical examples of the 28 ISFET sites provided on the wafer.

In the production of individual ISFET chips from a wafer, the individual ISFET sites, such as sites 1 and 2, will be separated to form separate individual chips and hence individual sensors. This separation, such as along the line A—A of FIG. 1, for example, can be partially accomplished by V-groove etching at the boundary of the individual ISFET sites. For example, the V-groove etch on the boundary between sites 1 and 2 could be as shown by the sloping lines 31 bracketing that site boundary. During the V-groove etching process it is necessary to protect the back of the ISFET. This can be done by covering the back with a wax disc.

It will be evident that upon separation of the individual sites, there will be separate silicon mesas formed at the edges of the individual ISFET chips. The sidewalls of the mesas would, in the normal course of a header mounting of the ISFETs, expose the substrate to the solution to be measured by the ISFET. The particular solution to this problem decribed in U.S. Pat. No. 4,505,799 is as shown in FIG. 4 of that patent. It involves the coating of the sides of the mesas with an epoxy, which is applied during probe assembly. This means of protecting and isolating the mesa sides has, however, been found to be difficult and uneconomical, for it must be done in the chip stage of the production process, which means that each chip would have to be processed separately.

The present invention utilizes a method for the passivation of the chip edges in the wafer stage of production, thereby making batch processing more practical in that a plurality of chips may be done in one operation. Not only is the proposed method less expensive than the previous method, it also makes possible improved mounting and packaging of the ISFETs in probe assemblies as may be required to produce a rugged probe for making measurements.

Figure 4:
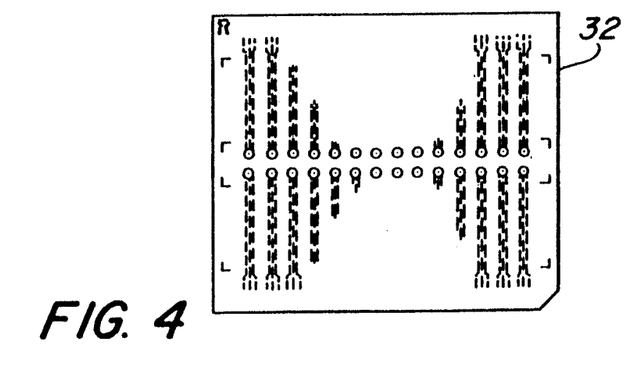
FIG. 4 is a plan view of the top of the glass carrier to which the substrate is bonded.

In the proposed method, the silicon wafer 12 of FIG. 3 is anodically bonded to a borosilicate glass carrier 32, shown in FIG. 4. That carrier has holes positioned in correspondence to the ISFET sites of wafer 12. The holes are of diameter sufficient to maintain uncovered the contact pads of the individual ISFET sites. Conductive paths or lead-outs are deposited on the glass carrier between connecting pads on opposite edges of the carrier to the areas adjacent the holes in order to provide a means for making an electrical connection from the ISFETs to an edge of the carrier.

Figure 5:
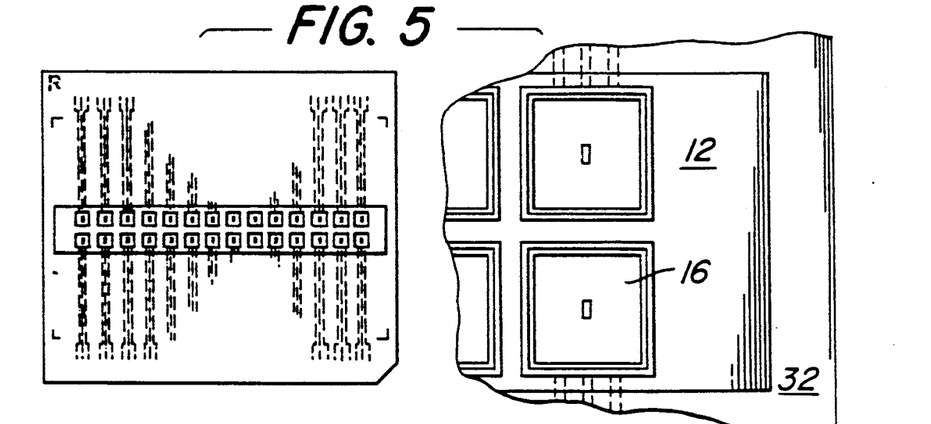
FIG. 5 is a plan view of the top of the combination of the substrate and the carrier.

A top view of the combination of the wafer 12 and the carrier 32 is shown in FIG. 5. This figure also shows a blowup of two sites, giving a top view of the sites after the V-groove etch along the site boundaries has been accomplished.

Figure 8:
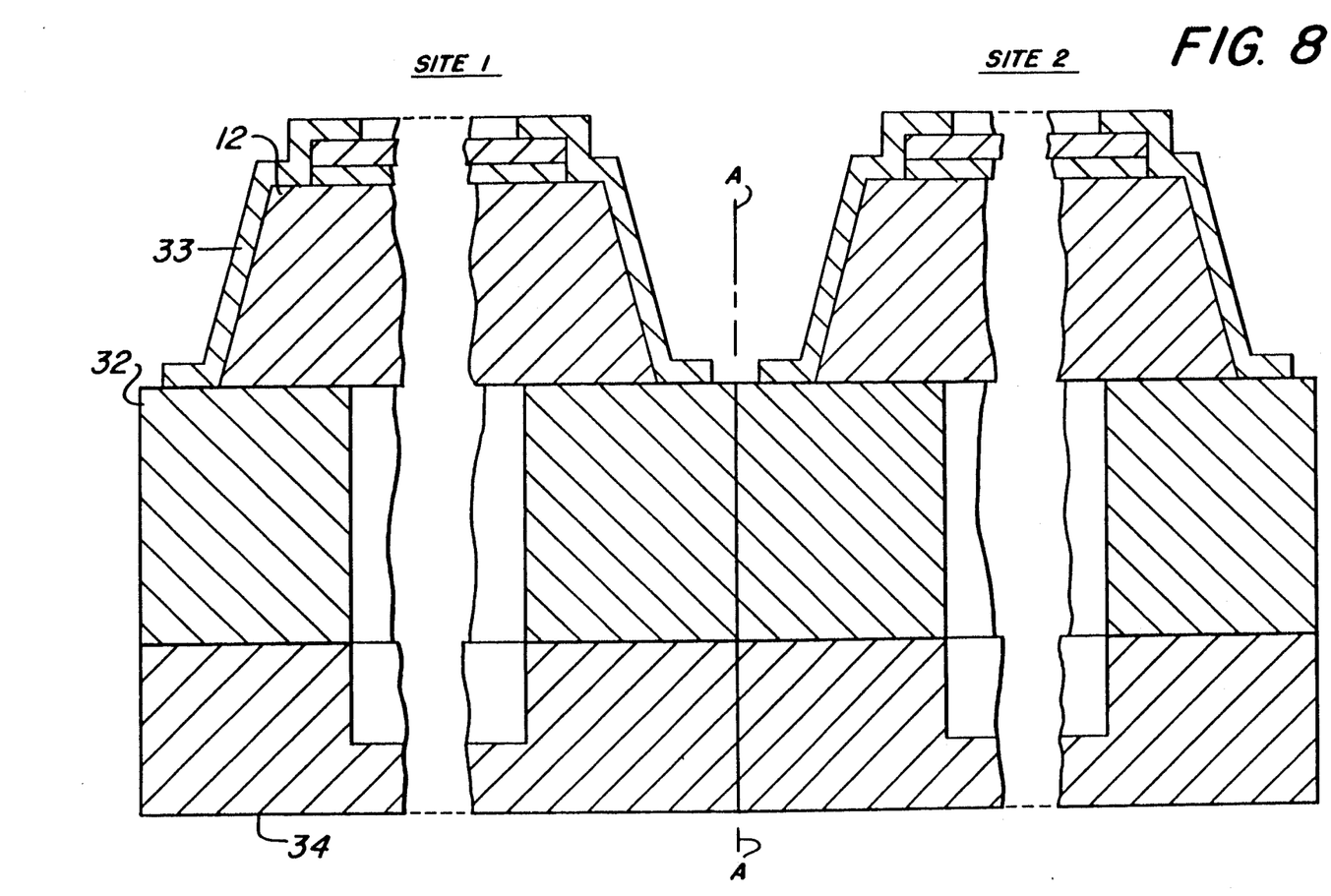
FIG. 8 is a cross-section of two ISFET sites after the substrate, the carrier and the cover have been bonded and V-groove etching has isolated the sites into separate mesas whose sidewalls have been passivated.
Figure 9:
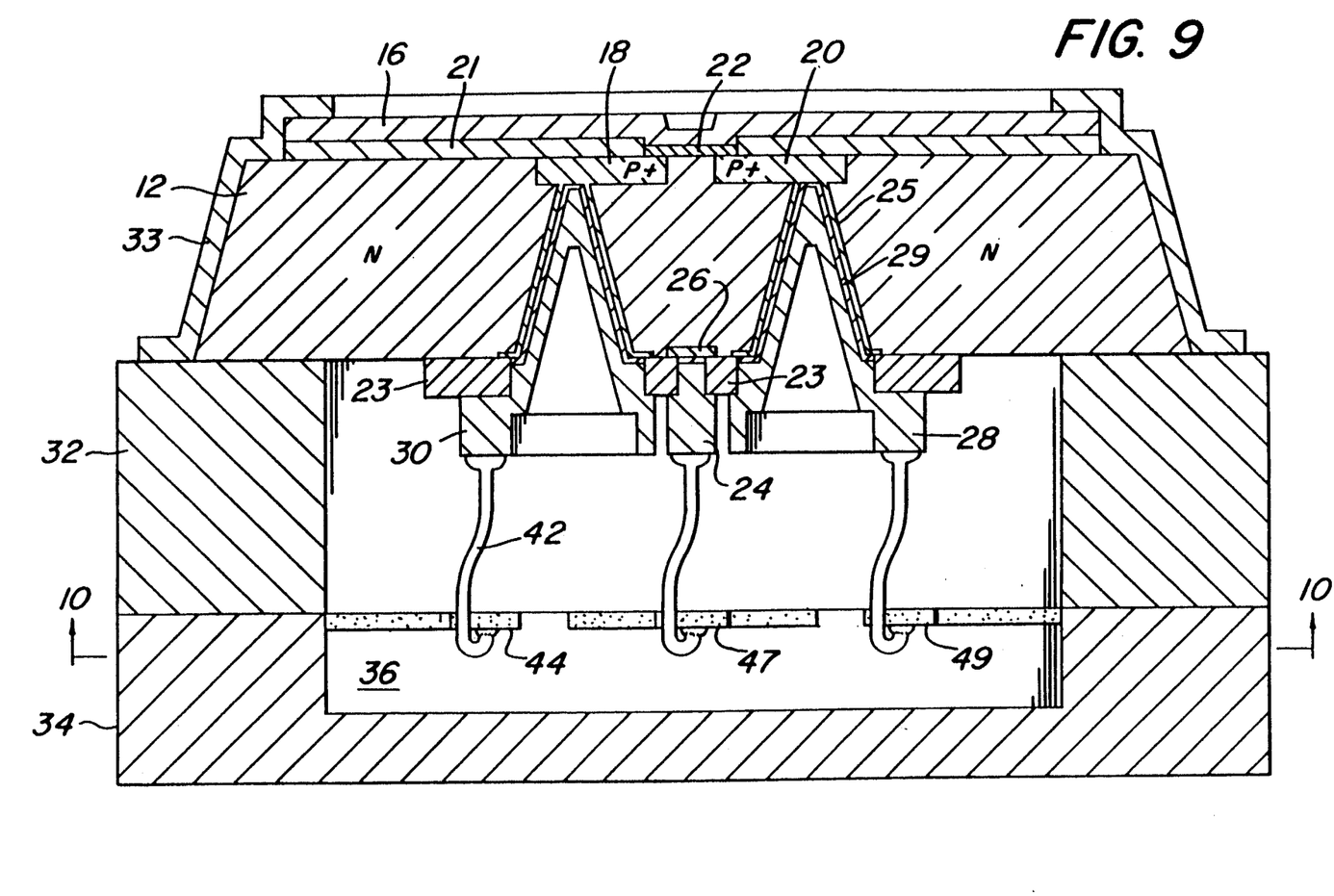
FIG. 9 is a cross-section of a completed structure in which a single ISFET is mounted on a header, which comprises the carrier and the cover, and in which the electrical connections have been completed.

In order to passivate the mesa edges formed by the V-groove etching of the individual ISFET sites in the wafer stage, a passivation coating 33 of $Ta_2O_5$ is applied over the edges only, as shown in FIGS. 8 and 9.

Figure 6:
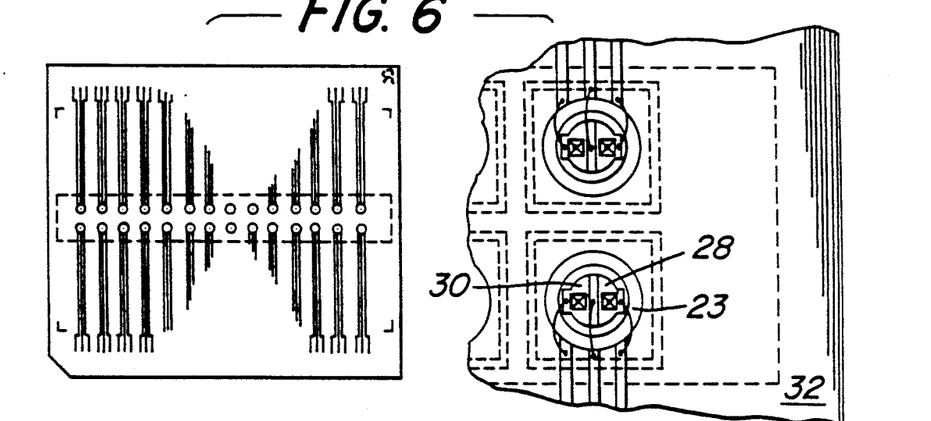
FIG. 6 is a plan view of the bottom of the combination of the substrate and the carrier.

FIG. 6 shows a bottom view of the carrier-wafer combination of FIG. 5, and shows, in the blowup at the right, details of the connections made between the metallized conductive paths forming the lead-outs and the pads of the individual ISFETs.

Figure 7:
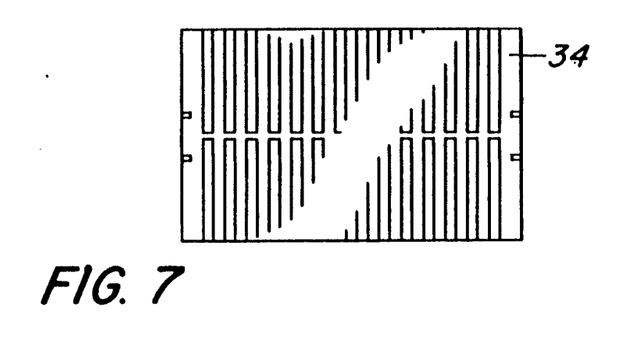
FIG. 7 is a plan view of the top of the cover which is used to cover the lead-outs on the bottom of the carrier as well as the back contacts of the ISFET sites.

A silicon cover plate is used to protect the electrical lead-outs. The cover plate is shown in FIG. 7, which shows the channels 36, which are etched into the cover so as to accommodate the metallized leads on the carrier bottom without the possibility of shorting those leads. After the contact pads 24, 28 and 30 have been wire bonded to the metallized leads deposited on the bottom of the carrier, as shown in FIG. 8, the silicon cover 34 is anodically bonded to the bottom of the carrier so that the combination, which constitutes a plurality of header mounted ISFETs, has a cross-section, as shown in FIG. 8 for sites 1 and 2. The combination is then diced into 28 individual header mounted ISFET structures, each of which has a cross-section as shown in FIG. 9.

Figure 10:
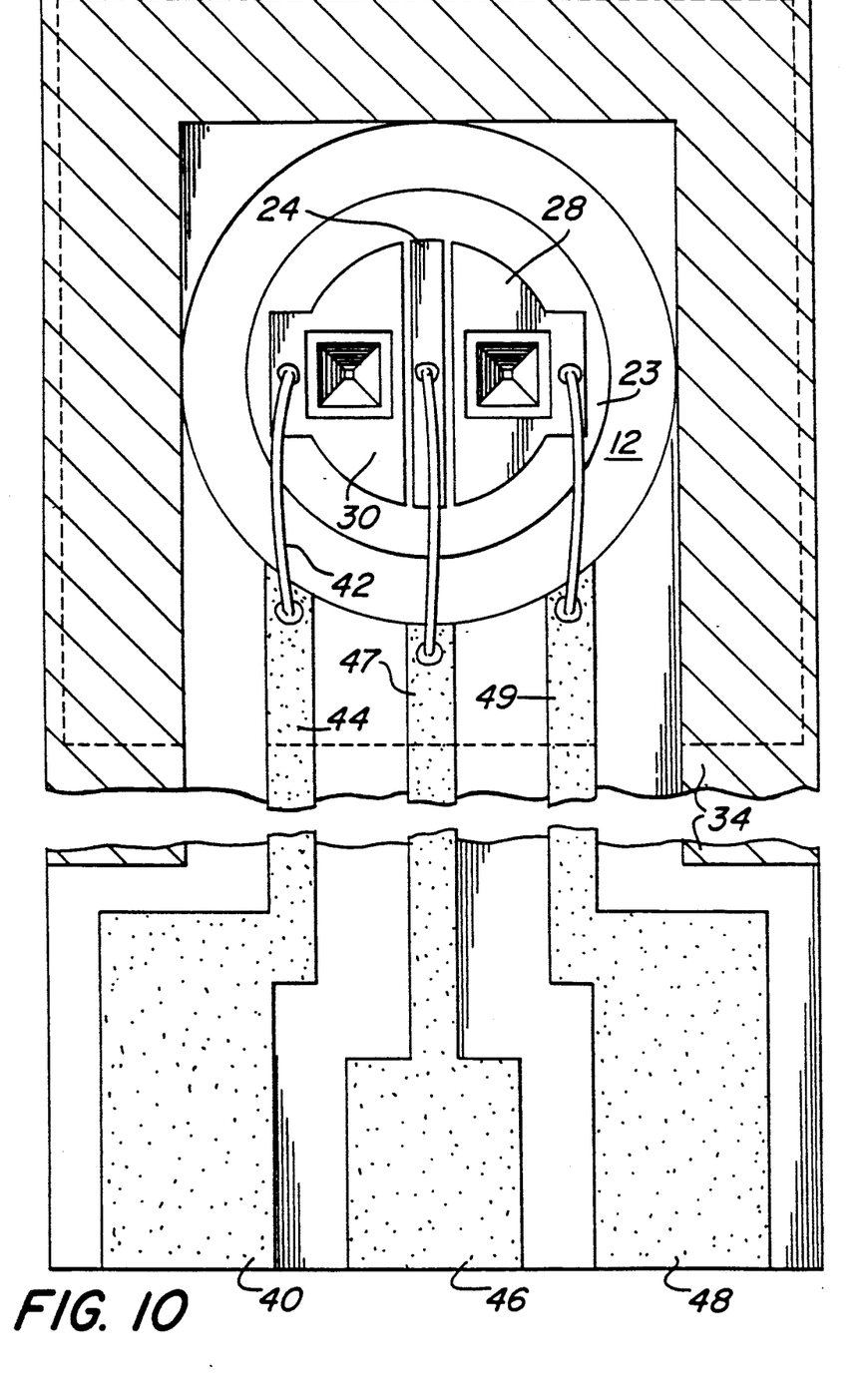
FIG. 10 is a plan view of the bottom or back of the single, header mounted ISFET of the invention.

A plan view of the bottom of a single ISFET structure with the cover removed is shown in FIG. 10 to illustrate the manner in which the lead-outs or electrical connections are taken from the ISFET pads to connection pads at the edge of the structure. Thus the drain 18 is connected to the pad 40 by way of the drain connecting pad 30, the wire 42, which is wire bonded to the pad 30 and to the metallized lead strip 44, which is the lead-out which connects to connection pad 40. The substrate is similarly connected to the pad 46, by way of metallized strip 47, and the source is connected to pad 48 by way of strip 49.

Figure 11:
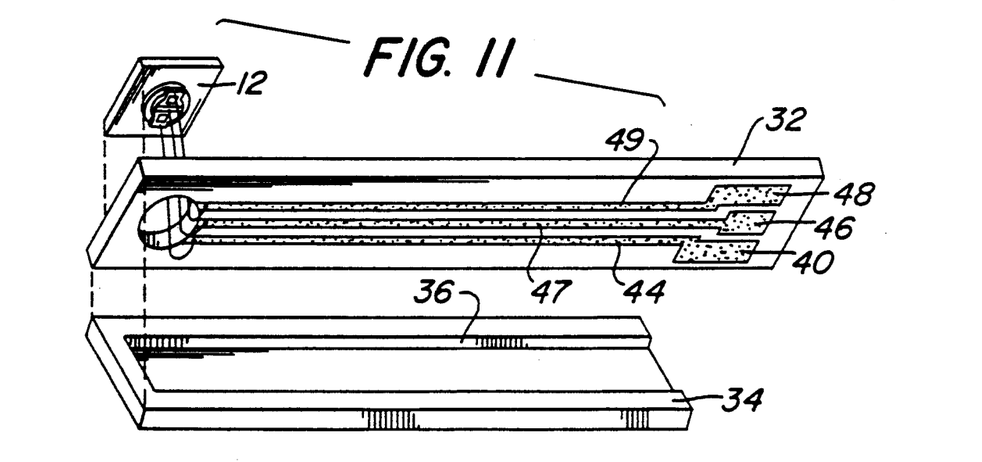
FIG. 11 is an exploded view of the complete header mounted ISFET which omits details of the passivation coating of the sidewalls.

In FIG. 11, there is shown an exploded view of the complete assembly of a single, header mounted ISFET structure.

What is claimed is:

1. A method for producing a header mounted solid state sensor structure for an immersible probe assembly so that it will environmentally interface the material to be tested by protecting the contacts and the sidewalls of the sensor from that material, comprising the steps of:

providing a plurality of sensor sites on a semiconductor substrate, said sites each having a chemically sensitive region on the front of said substrate and electrical contact pads on the back of the substrate, said contact pads being connected to the sensor structure;

providing a carrier for said substrate;

bonding the back of said substrate to said carrier at the periphery of said contact pads;

V-groove etching the substrate at the boundaries of the individual sensor sites to form isolated substrate mesas each representing an individual sensor structure;

deposition of a passivation coating over the sidewalls of the substrate mesas in a manner which will not obviate the sensitivity of the chemically sensitive region;

providing electrical lead-outs from said contact pads of the sensor to corresponding contact areas on the carrier arranged for connection to outside circuits; and dicing the wafer at the site boundaries to produce individual header mounted solid state sensor structures.

2. The method of claim 1 in which the substrate is silicon and the carrier is borosilicate glass, which is bonded to the substrate by an anodic bonding process.

3. The method of claim 2 in which the combination of the substrate and the carrier is anodically bonded to a silicon cover having a channel for accommodating each set of lead-outs.

4. A method for producing a plurality of header mounted chemically sensitive ISFET structures for immersible test probe assemblies such that the contacts and the sidewalls of the ISFETs will be protected from the chemicals to be tested, comprising the steps of:

providing a plurality of electrochemically sensitive ISFET sites on a semiconductor substrate, said sites each having a source region, a drain region and an electrochemically sensitive gate region on the front of said substrate and a group of contact pads including a substrate contact pad, a drain contact pad and a source contact pad on the back of the substrate;

providing a carrier for said substrate;

bonding said substrate to said carrier at the periphery of each of said groups of contact pads;

V-groove etching the substrate at the boundaries of the individual ISFET sites to form isolated silicon mesas each representing an individual ISFET structure; deposition of a passivation coating over the front of the substrate in a manner which will not obviate the chemical sensitivity of the gate regions;

providing electrical lead-outs from said contact pads of the ISFETs to corresponding contact areas on the carrier arranged for connection to outside circuits; and dicing the wafer at the site boundaries to produce individual header mounted chemically sensitive ISFET structures for probe assemblies.

5. The method as set forth in claim 4 in which the carrier is a borosilicate glass and the substrate is anodically bonded to said carrier.

6. A method for producing header mounted chemically sensitive ISFET structures for immersible test probe assemblies such that the contacts and the sidewalls of the ISFETs will be protected from the chemicals to be tested, comprising the steps of:

providing a plurality of electrochemically sensitive ISFET sites on a semiconductor substrate, said sites each having a source region, a drain region and an electrochemically sensitive gate region on the front of said substrate, a substrate contact pad on the back of said substrate and individual holes leading from the back of the substrate to the source and drain regions with contact between the respective source and drain regions and corresponding contact pads on back of the substrate being provided through a metallized coating on the sidewalls of the holes, said metallized coating being dielectrically isolated from said substrate;

providing a glass carrier for said substrate, said glass carrier having a composition such that it has a thermal coefficient closely matching that of the substrate and a structure such that it has holes therein and metallized electrical lead-outs thereon such that the location of said holes will match the location of the ISFET sites when the back of the substrate is placed in registration with the carrier to thereby maintain uncovered the contact pads associated with the ISFET sites and enable said lead-outs to provide electrical access to the area of the holes from the edges of said carrier;

anodically bonding the back of said substrate to said glass carrier at the periphery of the contact pads associated with each of said ISFET sites;

V-groove etching the boundaries of the individual ISFET sites to form isolated silicon mesas each representing an individual ISFET structure;

deposition of a passivation coating over the sidewalls of the etched substrate in a manner which will not obviate the chemical sensitivity of the gate regions;

providing electrical contact from said contact pads of each of the ISFET sites to the corresponding metallized electrical lead-outs of the carrier; and dicing the wafer at the site boundaries to produce individual chemically sensitive ISFET structures on glass carriers suitable to form headers for probe assemblies.

7. The method of claim 6 which includes prior to the dicing step the step of attaching to the back of said carrier a silicon plate having channels to accommodate the electrical lead-outs of the carrier without shorting them, said bonding being at least along the periphery of said channels to provide protection for the back of the associated ISFET and its electrical lead-outs.

8. The method of claim 7 in which the method of attaching a silicon plate to the back of said carrier includes anodically bonding said plate and said carrier.

* * * * *